(12) United States Patent
Jibu

(10) Patent No.: US 6,780,978 B2
(45) Date of Patent: Aug. 24, 2004

(54) FLUORESCENCE-ACTIVATING ANTISERA AND IGG FRACTION THEREFROM

(75) Inventor: Masaki Jibu, Hamamatsu (JP)

(73) Assignee: Hamamatsu Photonics, K.K., Shizuoka-ken (JP)

( * ) Notice: Subject to any disclaimer, the term of this patent is extended or adjusted under 35 U.S.C. 154(b) by 55 days.

(21) Appl. No.: 10/151,437

(22) Filed: May 21, 2002

(65) Prior Publication Data

US 2003/0065150 A1 Apr. 3, 2003

Related U.S. Application Data

(62) Division of application No. 09/003,710, filed on Jan. 7, 1998, now Pat. No. 6,437,099.

(51) Int. Cl.[7] .......................... C07K 16/06; C07K 16/44
(52) U.S. Cl. ................. 530/389.8; 436/800; 530/388.9; 530/807
(58) Field of Search ........................... 530/388.9, 389.8, 530/807, 389.3; 436/800

(56) References Cited

U.S. PATENT DOCUMENTS

| 4,444,317 A |   | 4/1984 | Wick et al. .................. 209/3.1 |
| 5,447,838 A |   | 9/1995 | Meiklejohn et al. ........... 435/5 |
| 5,994,143 A | * | 11/1999 | Bieniarz et al. ............... 436/91 |
| 6,037,152 A |   | 3/2000 | Richards et al. ........... 435/91.2 |
| 6,437,099 B1 | * | 8/2002 | Jibu ........................ 530/389.8 |

OTHER PUBLICATIONS

Bell et al. Chem Phys Lett. vol. 221, pp 15–22 (04/94).
Indig et al. Biophys. J. vol. 61, pp 631–638 (03/92).
Mukkur, T.K.S. CRC Crit Rev Biochem. vol. 16(2), pp 133–167 (1984).
Nishikawa, et al., Fluorescent/Phosphorescent Method—Chemical Structure and Fluorescence, Kyoristu Publication Co., Ltd., pp. 32–33, 1984.
Nishikawa, et al., fluorescent/Phosphorescent Method—How to Execute Fluorescence Analysis, Kyoristu Publication Co., Ltd., p. 49, 1998.
Ohkawa, et al., Pigment Handbook, Kodansha Scientific (1986), pp 346–379.

* cited by examiner

*Primary Examiner*—David Saunders
(74) *Attorney, Agent, or Firm*—Pillsbury Winthrop LLP

(57) ABSTRACT

This invention allows the fluorescence analysis of a nonfluorescent dye with high specificity and high sensitivity by virtue of the formation of a complex among an antibody directed against an immunogen having the nonfluorescent dye, an antiserum containing the antibody, and the nonfluorescent dye, which is an IgG fraction of the antibody, as well as, of the manifestation of fluorescent ability of the dye, which would otherwise be nonfluorscent, resulting from the formation of the complex. Also, the invention enables higher sensitivity in fluorescence measurement where the background fluorescence is less, by employing Malachite Green which will turn into a fluorescent dye.

12 Claims, 12 Drawing Sheets

MG-KLH : ANTIGEN (HEMOCYANIN LABELED WITH MALACHITE GREEN)
KLH : HEMOCYANIN
MG-BSA : BOVINE SERUM ALBUMIN LABELED WITH MALACHITE GREEN
BSA : BOVINE SERUM ALBUMIN (1) MG (4 μM) ALONE
(2) MG + BLANK IgG
(3) MG + IgG FRACTION FROM ANTI-MG-KLH SERUM (GUINEA-PIG1)
(4) MG + IgG FRACTION FROM ANTI-MG-KLH SERUM (GUINEA-PIG2)

{MG + IgG FRACTION FROM ANTI-MG-KLH SERUM
(GUINEA-PIG1) }- {MG + BLANK IgG}

EXCITATION WAVELENGTH OF 617nm
FLUORESCENCE WAVELENGTH OF BETWEEN 630nm AND 800nm

FLUORESCENCE-ACTIVATING ANTISERA AND IGG FRACTION THEREFROM

CROSS REFERENCE TO RELATED APPLICATIONS

This patent document is a divisional of U.S. patent application Ser. No. 09/003,710 flied Jan. 7, 1998 and now U.S. Pat. No. 6,437,099, the content of which is incorporated herein by reference in its entirety.

BACKGROUND OF THE INVENTION

1. Field of the Invention

This invention relates to an antiserum, antibody, and IgG fraction which are directed against an antigen that is a substantially nonfluorescent dye, and which upon mixing with the dye turn it fluorescent.

2. Related Background Art

Spectroscopic analysis is conventionally in frequent use for analyzing a minute amount of substances in biological metabolites, or contaminants in the environment. Especially, absorption spectrum analysis and fluorescence spectrum analysis are widely employed because their methods of measurement are simple.

Although the absorption spectrum analysis has lower sensitivity in detection as compared with the fluorescence spectrum analysis (hereinafter referred to as "fluorescence analysis") which will be described in detail below, it has been more widely utilized because the subject substances to be detected often possess light absorption in the ultraviolet-visible region.

In absorption spectrum analysis, absorbance and a concentration of the subject substance to be detected are expressed according to the following equation:

$$\text{Absorbance} = \log(I_0/I) = \epsilon c l$$

where $I_0$ is the intensity of incident light, $I$ is the intensity of light that has transmitted through a sample, $\epsilon$ is the molar absorption coefficient of a subject substance to be detected, and $l$ is an optical path length.

As the equation shows, the measurement of absorbance provides for the ratio of intensity of the incident light to that of the transmitted light, which does not vary with an increase in the intensity of a light source or in the sensitivity of a detector.

In contrast, if the subject substance to be detected is fluorescent, fluorescence analysis may be utilized. In this case, since the quantity of light to be emitted by the subject substance when it is exposed to excitation light is measured, this enables the sensitivity of measurement to be improved by employing a stronger light source or increasing the sensitivity of the detector.

Specifically, the intensity (F) of light emitted as fluorescence, the concentration (c) of a fluorescent substance, and the intensity ($I_0$) of excitation light (or incident light) are correlated with each other, and the intensity (F) is proportional to the intensity ($I_0$) of the incident light as follows:

$$F = \Phi I_0 (1 - 10^{-\epsilon c l})$$

where $I_0$ is the intensity of incident light, $\epsilon$ is the molar absorption coefficient of a subject substance to be detected, $l$ is an optical path length, and $\Phi$ is a fluorescence quantum yield.

In cases where the subject substance to be detected is included in a sample, which is a mixture comprised of many components, it often happens that the absorption spectra of the contaminants may overlap those of the subject substance during the measurement of absorbances. This results in difficulty selectively measuring only the absorbance of the subject substance.

On the other hand, even in the case where the subject substance to be detected is included in a sample, which is a mixture comprised of many components, in fluorescence analysis, contaminants that are not fluorescent can be ignored. It is possible to selectively measure only the fluorescence of the subject substance by choosing the excitation and fluorescence wavelengths when fluorescent contaminants are coexistent in the sample.

For these reasons, fluorescence analysis is superior to absorption spectrum analysis in terms of the sensitivity in detection, as well as, of the possibility of measuring a mixture.

Therefore, in an analytical technique where the advantage that fluorescence analysis allows a high-sensitivity measurement, is combined with the high selectivity of an antigen-antibody reaction, antibodies directed against fluorescent dyes are conveniently prepared. When these antibodies are reacted with the dyes, they either decrease or increase the fluorescence intensities of the dyes.

Accordingly, based on the variations in fluorescence intensity, quantitative analysis specific to these dyes have been carried out.

However, there has been an inherent limitation to the high sensitivity, highly selective fluorescence analysis employing the aforementioned antigen-antibody reaction in that it is not applicable in the case where the subject substance to be detected is substantially nonfluorescent.

It is also known that a dye which is substantially non-fluorescent under normal conditions of measurement may turn fluorescent (i.e., acquire fluorescent ability) under specific conditions, thereby enabling fluorescent measurement.

For example, while Malachite Green (hereinafter referred to as "MG") is normally nonfluorescent, it is known to turn fluorescent in glycerin. There has been an explanation concerning this phenomenon that the rotations in a molecule of the dye is restricted under the influence of a solvent or the like and as a result, the dye molecule turns fluorescent.

Many fluorescent substances do exist in vivo and the fluorescence of these substances (autofluorescence) forms a background in the measurement of fluorescence of a biological sample, which may result in a decline in the sensitivity of detection. Also, in the measurement of immunofluorescence (hereinafter referred to as "fluoroimmunoassay") employing titer plates, fluorescence emitted by plastic materials of the titer plate similarly forms a background, which may result in a decline in the sensitivity of detection. These are the causes that preclude fluorescence measurement with high sensitivity in the prior art.

SUMMARY OF THE INVENTION

In consideration of the foregoing, an object of this invention is to provide an antibody capable of enhancing or manifesting its fluorescent ability by specifically binding to a dye which is substantially nonfluorescent under normal conditions of measurement and by restricting the rotations in a molecule of the dye owing to the binding. Also, an object of this invention is to provide an antibody capable of binding to a dye that enables the measurement with higher sensitivities as compared with other dyes because of its extremely low background fluorescence.

The invention provides an antiserum which comprises an antibody directed against an antigen having a substantially nonfluorescent dye, wherein a mixture of the antiserum or antibody and the dye is provided with fluorescent ability.

Further, the invention provides an IgG fraction which comprises a fraction derived from an antiserum containing an antibody directed against an antigen that has a substantially nonfluorescent dye, wherein a mixture of the IgG fraction and the dye is provided with fluorescent ability.

Also, the invention provides the antiserum as described above wherein the antigen is formed by conjugation of an immunogenic substance with the dye.

In addition, the invention provides the IgG fraction as described above wherein the antigen is formed by conjugation of an immunogenic substance with the dye.

Furthermore, the invention provides the antiserum as described above wherein the immunogenic substance is at least one member selected from the group consisting of bovine serum albumin, human serum albumin, egg albumin, bovine γ globulin, equine serum globulin, human γ globulin, ovine γ globulin, bovine thyroglobulin, porcine thyroglobulin, hemocyanin, and a synthetic polypeptide.

Also, the invention provides the IgG fraction as described above wherein the immunogenic substance is at least one member selected from the group consisting of bovine serum albumin, human serum albumin, egg albumin, bovine γ globulin, equine serum globulin, human γ globulin, ovine γ globulin, bovine thyroglobulin, porcine thyroglobulin, hemocyanin, and a synthetic polypeptide.

Still further, the invention provides the antiserum as described above wherein the dye has a triphenylmethane moiety.

Also, the invention provides the IgG fraction as described above wherein the dye has a triphenylmethane moiety.

Also, the invention provides the antiserum as described above wherein the dye having the triphenylmethane moiety is Malachite Green.

Also, the invention provides the IgG fraction as described above wherein the dye having the triphenylmethane moiety is Malachite Green.

Further, the invention provides the antiserum as described above wherein the dye has a diphenylmethane moiety.

Also, the invention provides the IgG fraction as described above wherein the dye has a diphenylmethane moiety.

Also, the invention provides the antiserum as described above wherein the dye having the diphenylmethane moiety is Auramine O.

Also, the invention provides the IgG fraction as described above wherein the dye having the diphenylmethane moiety is Auramine O.

According to the invention, an antibody directed against an antigen which is a substantially nonfluorescent dye is prepared and the antibody and the dye are mixed, thereby allowing the substantially nonfluorescent dye to turn fluorescent and enabling the fluorescence analysis of the dye in minute quantities. Further, the use of MG in the fluorescence measurement can reduce the background level to a great extent as compared with the use of other dyes such as CCJV (9-(2-carboxy-2-cyanovinyl)julolidine) or fluorescein, enabling higher sensitivity in measurement.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS

Figure 1:
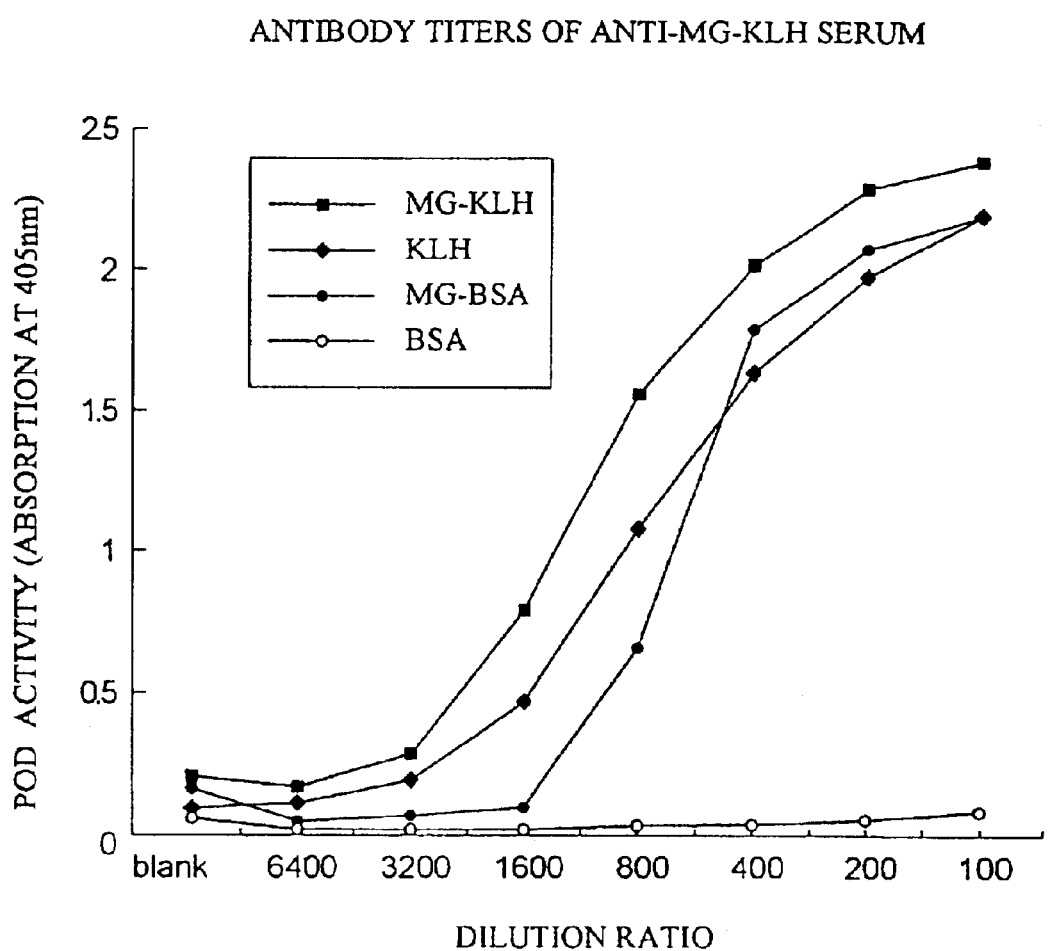
FIG. 1 represents a plot illustrative of antibody titers of the antiserum against hemocyanin labeled with Malachite Green according to this invention.

The invention will be explained in detail hereinafter.

(Substantially Nonfluorescent Dyes)

Dyes which can be used in this invention are not particularly limited insofar as they do not substantially exhibit fluorescence in ordinary solvents such as water, or are weakly fluorescent if they do exhibit fluorescence.

As used herein to describe the invention, the term, "substantially nonfluorescent" refers to dyes that do not exhibit fluorescence under ordinary conditions of measurement, or only exhibit extremely weak fluorescence; namely, they are regarded as substantially incapable of being fluorometrically analyzed by a commercially available device. See, Taiji Nishikawa et al., Fluorometric and Phosphometric Analysis; Kyoritsu Publishing: 1984; p. 30.

In this invention, where the fluorescence quantum yield of a dye is 1% or less under specified conditions, the dye falls within the meaning of "substantially nonfluorescent dyes" as used herein. Furthermore, where the fluorescence quantum yield of a dye is $10^{-2}\%$ or less under the specified conditions, the dye is definitely one of the "substantially nonfluorescent dyes".

In the invention, a dye which is substantially nonfluorescent turns fluorescent by a treatment according to the invention and becomes fluorometrically detectable; it means that the fluorescence quantum yield of the dye changes greatly (e.g., 1% or greater) upon interaction with an antibody by the treatment according to the invention, although its fluorescence quantum yield is extremely small under normal conditions of measurement (e.g., 0.01% or less). Of note is that this also applies to the cases where some special conditions of measurement, measuring devices or the like enable extremely weak fluorescence to be detected.

The dyes which can be used for the invention also include those that are fluorescent in an ordinary solvent such as water (implying that the fluorescence quantum yields are greater than 1%).

This particular case means that the fluorescence intensity of a dye further increases by virtue of the treatment according to the invention and it allows the analytical sensitivity to be greater than that obtainable by ordinary fluorescence analyses. As used herein, the phrase "increases in the fluorescence intensity" means that the fluorescence quantum yield will change to be greater.

In the invention, the increase in the fluorescence quantum yield as described above is preferably more than 10 times, more preferably 100 times, further preferably 1,000 times, and still further preferably 10,000 times.

For example, with Malachite Green its fluorescence quantum yield can be increased approximately over 1,000 times.

The dyes which can be used for the invention do not necessarily have absorption in the visible region (i.e., absorption maximum at a wavelength of greater than 350 nm), and include those having absorption in the ultraviolet region (i.e., absorption maximum at a wavelength of smaller than 350 nm) as well as those having absorption bands extended to the visible region.

Molecular structures of the dyes which can be used for the invention are not particularly limited, and possibly include those having a variety of chromophores.

Specifically, dyes containing chromophores stable in the vicinity of the neutral pH are preferred.

For example, dyes having a triphenylmethane skeleton in their molecular structures are particularly preferred. See, The Handbook of Dyes; Okawara, M., Ed.; Kodansha Scientific. More specifically, Malachite Green or the like, which is one of the dyes having a triphenylmethane skeleton in their molecular structures, is preferably used for this invention.

Also, dyes having a diphenylmethane skeleton in their molecular structures can be preferably used for the invention. See, The Handbook of Dyes, cited supra. Among dyes of the diphenylmethane type, an auramine type of dye can preferably be used; more specifically, the use of Auramine O is preferred.

(Immunological Substances)

Immunological substances which can be used for this invention are not particularly limited.

Generally usable substances, such as albumins (bovine serum albumin and human serum albumin), egg albumin, serum globulins (bovine γ globulin, equine serum globulin, human γ globulin, and ovine γ globulin), thyroglobulins (bovine thyroglobulin and porcine thyroglobulin), hemocyanin and synthetic polypeptides, can preferably be used for the invention.

(Preparation of Antigen Having Substantially Nonfluorescent Dyes)

In this invention there is no limitation to the methods of preparing antigens having substantially nonfluorescent dyes.

For example, the immunological substances can be mixed with the substantially nonfluorescent dyes under stirring for a prescribed period of time and antigen fractions containing the dyes can be isolated using gel filtration chromatography.

Further, if necessary, it is possible to purify the fractions according to purification techniques employing an immunoreaction. See, Immunoassay An Introduction; Written by Ray Edwords; Translated by Kawashima, K.; Nanzando: 1987; p 70.

The concentrations of the thus obtained antigen having the dye can, for example, be quantified by the Lowry Method.

(Preparation Of Antisera)

Antibodies which can be used for this invention may preferably be prepared by immunological procedures.

Immune animals to be used are not particularly limited, but rabbits and guinea-pigs may preferably be employed.

Adjuvants which can be used for the invention are not particularly limited, but a Freund's incomplete adjuvant, aluminum adjuvant, etc. as generally available may preferably be employed.

Methods of immunoinjection which can be used for the invention are not particularly limited, but a subcutaneous or intraperitoneal injection may preferably be employed, for example, against a guinea-pig.

In the invention, for confirmation of the production of an antiserum and collection thereof, it will be possible to perform them by conducting, where necessary, additional immunization, preliminary collection of the antiserum, and measuring antibody titers of the antiserum.

In the invention, there is no particular limitation to the methods for separation of collected antisera, and ordinary techniques can be employed; for example, they include the separation of antisera by centrifugation after coagulating the collected blood. The specific antibody activity of the obtained antiserum directed against the antigen dye may preferable be measured by an enzyme immunoassay or the like. See, Methods for Measurement Using Biological Activities; The New Experimental Manual of Basic Biochemistry; Maruzen; Vol. 6; p 98.

(IgG Fractions)

In the invention, there is no particular limitation to the methods for purification of IgG fractions from antisera. Methods such as salting-out, gel filtration, and ion exchange chromatography may preferably be employed, and especially, the protein A method can preferably be used. The thus obtained IgG fractions can further be concentrated to be adjusted to prescribed concentrations by centrifugation.

(Fluorescence Spectrum Measurements)

According to the invention, the above-mentioned antiserum or antibody is mixed with the nonfluorescent dye to provide a mixed solution which turns fluorescent, and the fluorescence spectra of the resulting mixed solution can be measured by various techniques. See, Fluorometric and Phosphometric Analysis, cited supra; Chap. 2; pp. 49–99.

Specifically, it has been made possible to quantify only the fluorescence of the dye with high sensitivity, and without any interference by coexisting substances, by measuring differential fluorescence spectra between the mixed solution and a control mixture.

In the invention, the fluorescence quantum yield of fluorescence that will manifest depends on the dyes, immunogenic substances, immunized animals, immunization procedures, methods of separation and purification, etc.

Furthermore, according to the invention, the quantitative analysis of the dye is enabled by utilizing its fluorescent ability that will manifest. The limit of the quantitative analysis depends on the fluorescence quantum yield as described above.

(Triphenylmethane Type Dyes)

With respect to Malachite Green, the sensitivity in absorbance can be compared with the sensitivity in measurement of fluorescence in the following manner.

Malachite Green is dissolved in a phosphate-buffered saline (hereinafter referred to as "PBS") to prepare a series of dilutions in the concentration range of 4–4,000 nM.

Figure 6:
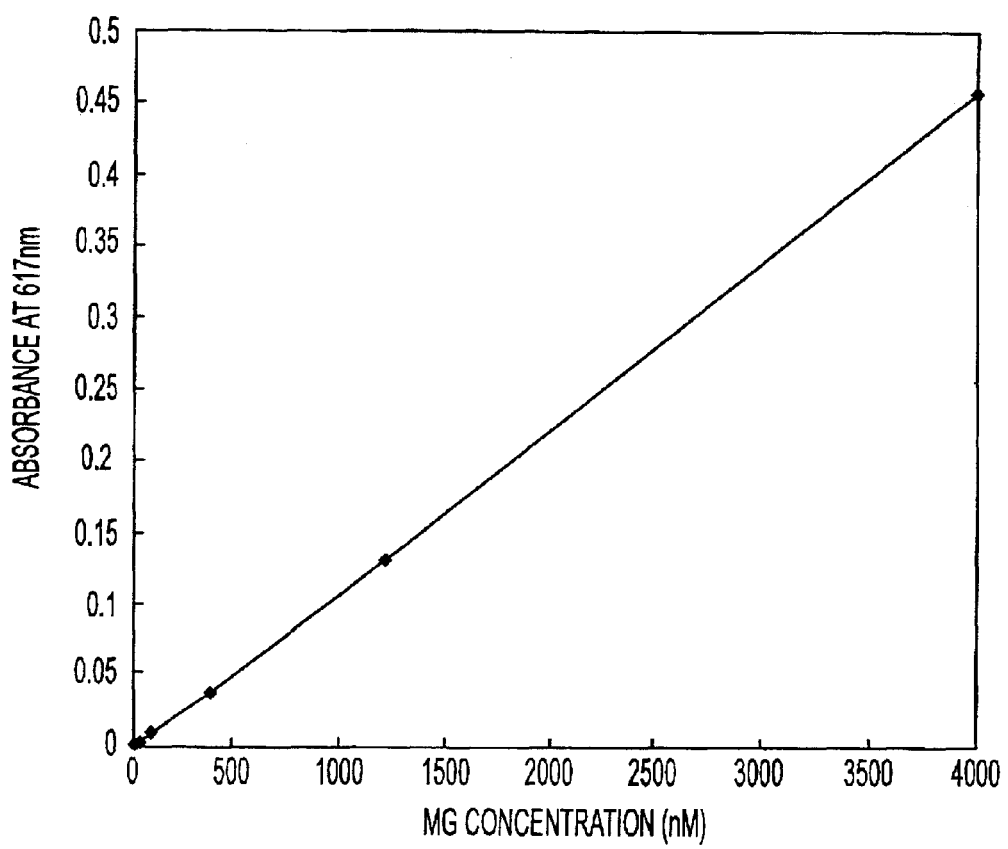
FIG. 6 represents a curve plot illustrative of concentrations of Malachite Green versus absorbances without IgG fraction according to this invention.

Absorbance at a wavelength of 617 nm in these dilutions is measured with a Hitachi Model 557 two wavelength spectrophotometer using a quartz cell with a 1 cm optical path length and PBS as the reference (See Table 1), and a concentration—absorbance curve is prepared (See FIG. 6).

TABLE 1

| Concentration (nM) | 4 | 12 | 40 | 120 | 400 | 1200 | 4000 |
|---|---|---|---|---|---|---|---|
| Absorbance (617 nm) | 0 | 0 | 0.002 | 0.009 | 0.036 | 0.132 | 0.464 |

As shown in the figure, a linear correlation between absorbances and concentrations is obtained in the concentration range of 40–4,000 nM, but absorbance can not be measured below concentration of 12 nM.

A series of dilutions of Malachite Green in PBS solutions are prepared by adding to the solutions, the IgG fraction according to the invention which has been derived from Guinea-pig 1 in certain amounts (with the final concentration being 0.2 $\mu$M), and by adjusting concentrations of the dye within the range of 0–12 nM.

Figure 5:
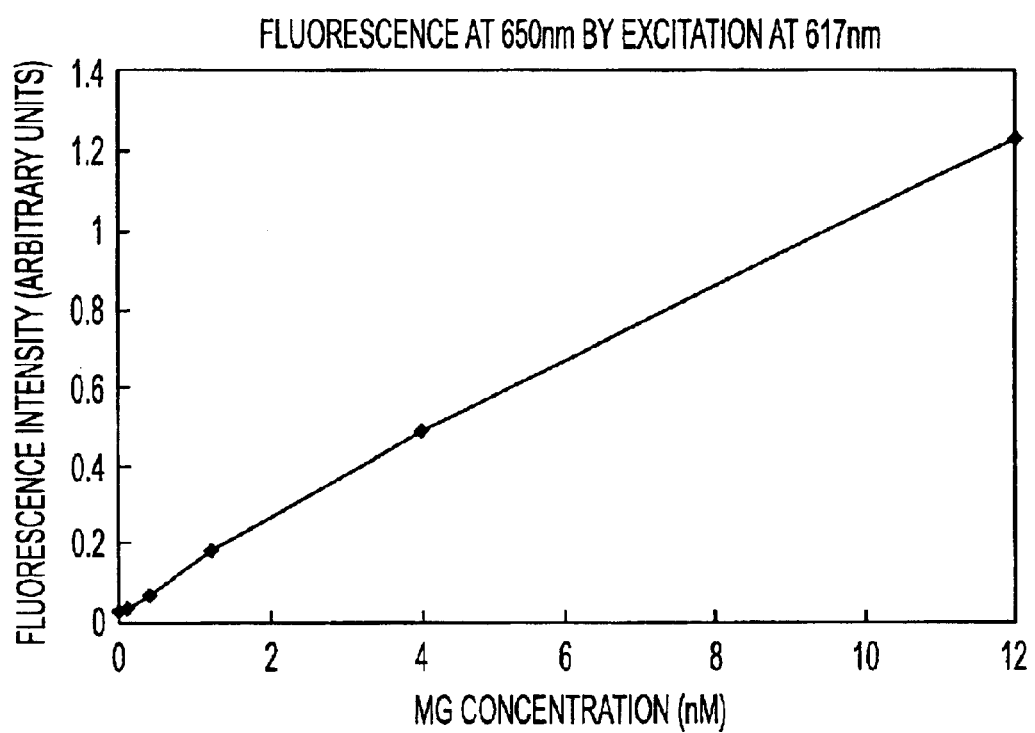
FIG. 5 represents a curve plot illustrative of concentrations of Malachite Green versus fluorescence intensities when Malachite Green at various concentration was mixed with the IgG fraction according to this invention.

Fluorescence of these dilutions is measured with a Hitachi Model 850 fluorescence spectrophotometer under the following conditions: in a quartz cell of optical path length of 1.0 cm at the excitation side; an excitation wavelength of 617 nm; an emission wavelength of 650 nm; a band-pass width of 5 nm at both excitation and emission sides; High gain of a photomultiplier; a time constant of 1.5 sec; and a fluorescence integration time of 30 sec. See Table 2. Thus, a concentration-fluorescence intensity curve is prepared (See FIG. 5).

The fluorescence intensity is expressed as output values (i.e., arbitrary, relative units) of the fluorescence spectrophotometer.

TABLE 2

| Concentration (nM) | 0 | 0.04 | 0.12 | 0.4 | 1.2 | 4 | 12 |
|---|---|---|---|---|---|---|---|
| Fluorescence intensity (650 nm) | 0.026 | 0.026 | 0.034 | 0.066 | 0.18 | 0.487 | 1.22 |

As shown in the figure, a linear correlation between fluorescence intensities and concentrations is obtained in the concentration range of 0.12–12 nM and this indicates that the quantitative analysis is possible within the concentration range.

Therefore, although the absorbance measurement as described above can not detect 12 nM, the fluorescence measurement using the antibody according to the invention allows the detection of a concentration of as low as 0.12 nM which is lower than 12 nM by a factor of two-order, with good quantification and high sensitivity; the sensitivity is about 300 times (40 nM/0.12 nM=300) the level obtained by the absorbance measurement.

(Diphenylmethane Type Dyes)

Figure 7:
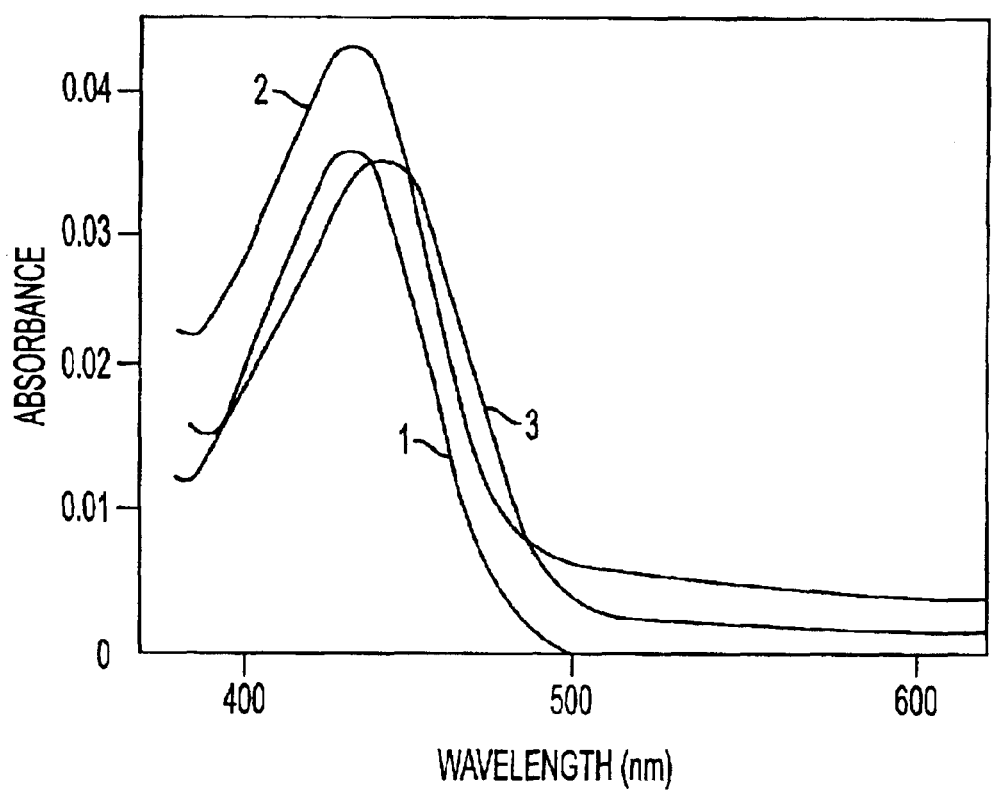
FIG. 7 represents absorption spectra of a mixture of the IgG fraction derived from the antiserum against hemocyanin labeled with Malachite Green according to this invention, and Auramine O.

In cases where Auramine O (hereinafter referred to as "AO"), which is one of the diphenylmethane type, is used, effects similar to Malachite Green are observed. Specifically, in the absorption spectra of AO, an anti-MG-KLH IgG mixed solution exhibits a decline in the absorption intensity, as well as a shift toward longer wavelengths (See FIG. 7).

Figure 8:
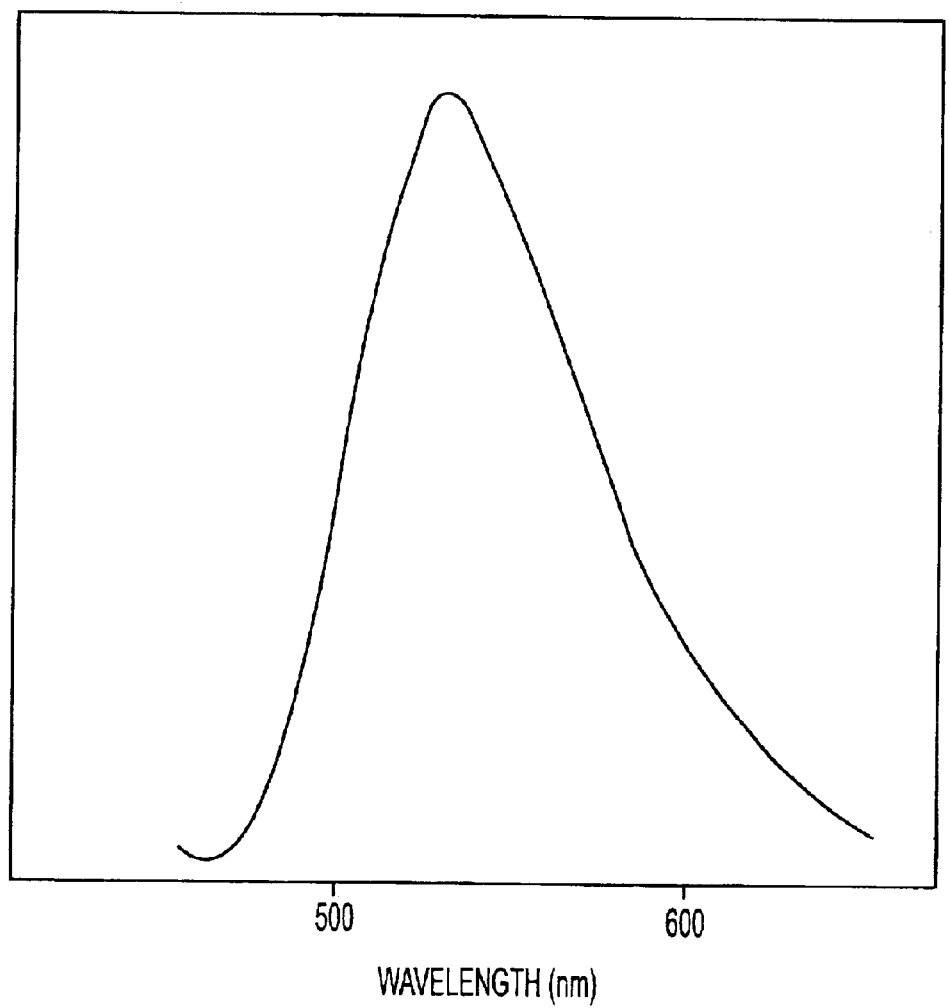
FIG. 8 represents a differential fluorescence spectrum of a mixture of the IgG fraction derived from the antiserum against hemocyanin labeled with Malachite Green according to this invention, and Auramine O.

Auramine O also manifests its fluorescent ability upon mixing with the anti-MG-KLH IgG (See FIG. 8). The fluorescence intensity of AO is assumed to be the same as Malachite Green.

Results as described above indicate that the anti-MG-KLH IgG according to the invention can at least recognize and combine with a diphenylmethane group in the dye molecule.

(Measurement Based On Low Background Fluorescence Employing Malachite Green)

Many fluorescent substances do exist in vivo. For example, retinol (vitamin A) emits fluorescence having a maximum around 470 nm, and riboflavin emits fluorescence having a maximum around 536 nm. See, The Dictionary of Biochemistry; Tokyo Kagaku Dojin; p. 1373 and p. 1350, respectively. The fluorescence of these substances (autofluorescence) may form a background in the fluorescence measurement of biological samples, which may result in a decline in the sensitivity of detection.

Also, in the case of measurement of immunofluorescence (or a fluoroimmunoassay) using titer plates, fluorescence emitted by plastic materials of the titer plate forms a background in like manner, which may result in a decline in the sensitivity of detection.

In these instances, if excitation and fluorescence wavelengths in the fluoroimmunoassay can be set either at a shorter wavelength or at a longer wavelength relative to the respective excitation and fluorescence wavelengths of the background fluorescence, its influence will effectively be diminished.

To that end, a fluorescent dye that has excitation and fluorescence wavelengths separated from those of the autofluorescence will become useful. For example, Malachite Green used for the invention is one of those preferred dyes.

In practice, it has been demonstrated that Malachite Green is a highly effective dye for use in the fluoroimmunoassay of serum components as will be described below. Namely, Malachite Green is covalently labeled to an antibody directed against the substance to be detected, an anti-MG antibody is reacted against the antibody, and thus it becomes possible to observe the fluorescence spectrum emitted by MG. Where the anti-MG antibody is used, MG labeled to the antibody is shown to be useful as a fluorescence label. Furthermore, the quantity of the background fluorescence pertaining to a sample (a variety of background fluorescence such as arising from titer plates) and the spectra when observed under MG's excitation wavelength are compared with those when observed under shorter excitation wavelengths, and it is found that only extremely low background fluorescence is observed in the case where the sample is labeled with MG and that higher sensitivity in measurement is enabled as compared with other dyes.

According to the invention, an antiserum containing an antibody directed against an antigen, which has a substantially nonfluorescent dye, as well as its IgG fraction separated; when this separated antiserum or IgG fraction is mixed with the dye, the dye molecules manifest, or enhance their fluorescent ability. By measuring fluorescence of this mixture, it becomes possible to carry out the microanalysis of the dye. When the anti-MG antibody is used, MG labeled to the antibody is shown to be useful as a fluorescence label.

Further, in cases where a sample is labeled with MG, the quantity of the sample's background fluorescence can effectively be reduced, thereby enabling higher sensitivity in measurement as compared with other dyes.

EXAMPLES

Referring to the appended drawings, examples according to the invention will be fully illustrated hereinafter.
(1) Preparation of Hemocyanin Labeled with MG and Bovine Serum Albumin Labeled with MG.

Hemocyanin (Keyhole Lympet Hemocyanin available from Calbiochem; hereinafter referred to as "KLH") 9.6 mg was dissolved in 10 ml of a 0.5 M carbonate buffer solution (pH 9.5) in a 10 ml Erlenmeyer flask. To this was added 6.5 mg of Malachite Green isothiocyanate (Molecular Probe Inc.; hereinafter referred to as "MGITC") and it was stirred a day and night at 4° C. under the shielded light.

The reaction solution as described above was applied to gel filtration chromatography (Econo-Pac 10 DG available from Bio-Rad; equilibrated with PBS) and KLH labeled with MG (hereinafter referred to as "MG-KLH") was separated from unreacted MGITC.

The protein concentration of the resulting KLH fraction labeled with MG was 220 $\mu$g/ml as determined by the Lowry Method.

Bovine serum albumin (hereinafter referred to as "BSA") 9.5 mg was dissolved in 10 ml of a 0.5 M carbonate buffer solution (pH 9.5) in a 10 ml Erlenmeyer flask. To this was added 6.5 mg of MGITC and it was stirred a day and night at 4° C. under shielded light.

The reaction solution as described above was applied to gel filtration chromatography (Econo-Pac 10 DG; equilibrated with PBS) and BSA labeled with MG (hereinafter referred to as "MG-BSA") was separated from unreacted MGITC.

The protein concentration of the resulting BSA fraction labeled with MG was 237 $\mu$g/ml as determined by the Lowry Method.
(2) Immunization of Experimental Animals
(i) Initial Immunization MG-KLH solution (1.0 ml) prepared according to Procedure (1) as described above was diluted with 1.0 ml of a physiological saline solution to give an antigen solution. This was injected to a RAS vial (Ribi Adjuvant System, Ribi) under sterilized conditions, using an injector (5 ml) with a 0.22 $\mu$m filter. Thereafter, this vial was vigorously shaken for two minutes to prepare an emulsion of the antigen solution and the adjuvant.

The resulting emulsion was administered to guinea-pigs (Hartley, female, SPF, n=3) at a dose of 0.5 ml per animal under anesthetization (using NEMBUTAL at a dose of 8 mg per animal); the animal was injected with each 0.1 ml of the emulsion subcutaneously on her rear back part at four sites, and with 0.1 ml of the emulsion intraperitoneally.

(ii) Additional Immunization

The animals were additionally immunized with the same antigen quantities and adjuvant as before, twice at three week intervals after the initial immunization.
(3) Measurement of Antibody Titer of Antisera
(i) Schedule of Antibody Titer Measurements The schedule of the antibody titer measurements was determined following a preliminary experiment as described below.

Two weeks after the first additional immunization, partial blood samples (0.5 ml per animal) were collected from the heart of the immunized animals and the antibody titers of the samples were measured. This confirmed that sufficient increases in the antibody titer were observed two weeks after the additional immunization.

As a result, whole blood samples were collected two weeks after the second additional immunization, and then the final antibody titers were measured in the same manner as described above.
(ii) Preparation of Antisera The collected blood was allowed to stand for one hour in an incubator at 37° C., and to promote the formation of blood clots. After contracting the clots by leaving them overnight at 4° C., an antiserum was separated from the clots by centrifugation.

The antibody activity of the thus obtained antiserum specific to MG was determined by an enzyme immunoassay as described below.
(iii) Enzyme Immunoassays A 150 $\mu$l of MG-KLH solution (equivalent to KLH 220 $\mu$g/ml) was dissolved in 15 ml of a 50 mM carbonate buffer solution (pH 9.6) and each of 96 wells made of plastics in an immunotiter plate (ELISA-PLATE Model F-form available from Greiner) was coated with 0.1 ml of the solution. The plate was allowed to stand overnight at 4° C. and to let MG-KLH adsorbed to the walls of the titer plate.

To each well of the titer plate was added a washing solution containing PBS and 0.05% TWEEN 20 in an amount of 0.1 ml per well, and then the solution discharged. This washing step was repeated three times. Subsequently, a blocking solution (1% gelatin in PBS) was added to each well in an amount of 0.1 ml per well and the titer plate was allowed to stand overnight at 4° C.

The plate was again washed with the washing solution in the same manner as described above. A diluted solution of the antiserum (a series of dilutions 100–6400-fold) and an antiserum (not diluted) from a non-immunized guinea-pig, which served as a control, were added to each well in an amount of 0.1 ml per well. The titer plate was allowed to stand for 6 hr at room temperature to effect an antigen-antibody reaction.

After washing with the aforementioned washing solution, a horseradish peroxidase-labeled goat anti-guinea pig IgG antibody solution (with the final concentration of 16 $\mu$g/ml; Cappel) was added to each well in an amount of 0.1 ml per well and the titer plate was allowed to stand overnight at 4° C. to effect a reaction between IgG derived from the antiserum and the enzyme antibody.

After washing with the aforementioned washing solution in a like manner, a substrate solution (ABTS Peroxidase Substrate System available from Kirkegaard & Perry Laboratories Inc.) was added to each well in an amount of 0.1 ml per well. The titer plate was heated for 10 min at 37° C. to allow the enzyme reaction to take place, and then a stop solution (1% SDS aqueous solution) was added. The titer plate was set on a plate reader (Model 3550, available from Bio-Rad) and absorbance at 405 nm was measured.

FIG. 1 illustrates an embodiment where the antibody titers of a serum from the whole blood samples taken one week after the second additional immunization were measured. Significant antibody activities are observed in the dilutions of up to 3200-fold as compared with the control.

While the sera exhibited the antibody activity against MG-BSA, they did not do so against BSA. This indicates that the antiserum according to the invention specifically recognizes MG.

(4) Purification of IgG Fractions

IgG fraction was purified from the antiserum obtained as described above using protein A. The antiserum (1 ml) was chromatographed on a column immobilized with protein A (a protein A column kit for purification of antibodies; Ampure PA Kit available from Amersham) to provide about 4 ml of IgG fraction.

The resulting IgG fraction was charged into a sample-pretreatment cartridge (ULTRACENT-10 for use in centrifugation; available from TOSO) at portions of 1–1.5 ml and centrifuged for 30–60 min at 4° C. under cooling at 5,000 rpm (×3,000 G). This procedure was repeated to concentrate the approximately 4 ml fraction to a final volume of 0.7 ml.

(5) Reaction of the Antibodies with MG

Employing bovine γ globulin as a standard sample, the protein content of the concentrated IgG fraction as obtained above was quantified with a Bio-Rad protein assay kit (Bio-Rad). The results are provided below:

| Guinea-pig | Total protein concentration of the serum | IgG fractions |
|---|---|---|
| 1 | 150 mg/ml | 6.15 mg/ml |
| 2 | 146 mg/ml | 7.83 mg/ml |

Figure 2:
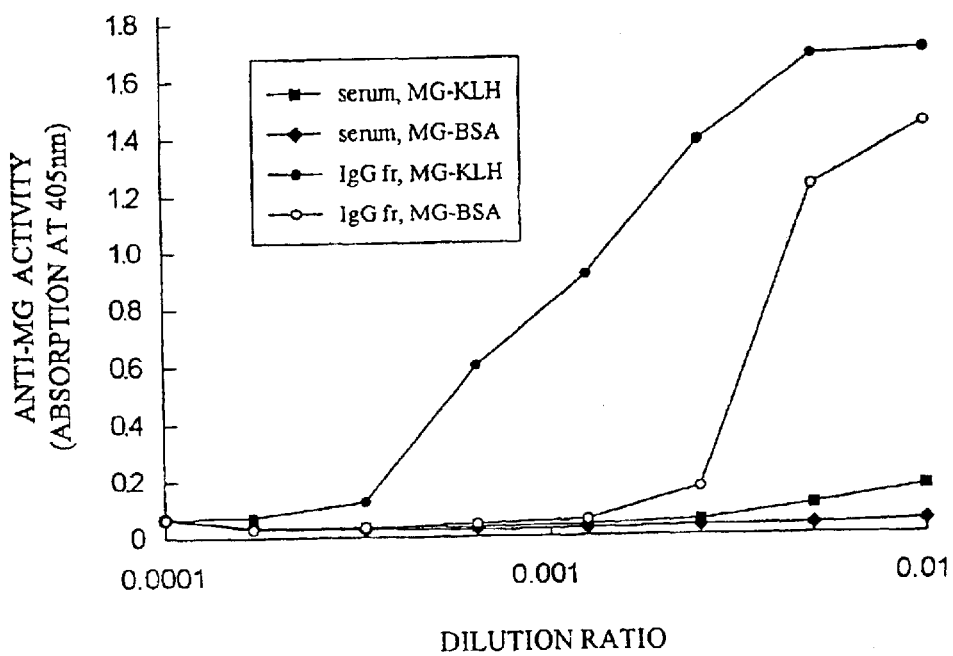
FIG. 2 represents a comparison of antibody activities of the antiserum according to the invention and of the IgG fraction according to the invention.

Based on these results, the antisera were diluted so that their protein concentrations equal to those of the IgG fractions. These diluted antisera and the IgG fractions were diluted to prepare the respective 100-fold–6,400-fold dilutions. Each dilution (0.1 ml) was added to each well of the 96 well immunotiter plate onto which MG-KLH and MG-BSA had been adsorbed and allowed to stand overnight at 4° C. to effect the antigen-antibody reaction. Subsequently, the enzyme immunoreaction was performed in a manner similar to that used for the measurement of antibody titers to compare the antibody activities of the antisera with those of the IgG fractions. As the results are shown in FIG. 2, it is found that the IgG fractions exhibit markedly higher activities than do the antisera and that the purification of the IgG fractions has resulted in increases in specific activities.

(6) Absorption Spectra

Concentrations of the aforementioned IgG fraction and MG solution were adjusted by dilution such that the protein concentration as described above and MG concentration would finally be 2 $\mu$M and 4 $\mu$M, respectively. Further, employing γ globulin of a guinea-pig as the control against anti-MG-KLH IgG (i.e., blank IgG), the absorption spectrum of a mixture of the IgG fraction and the MG solution was measured (See FIG. 3).

Figure 3:
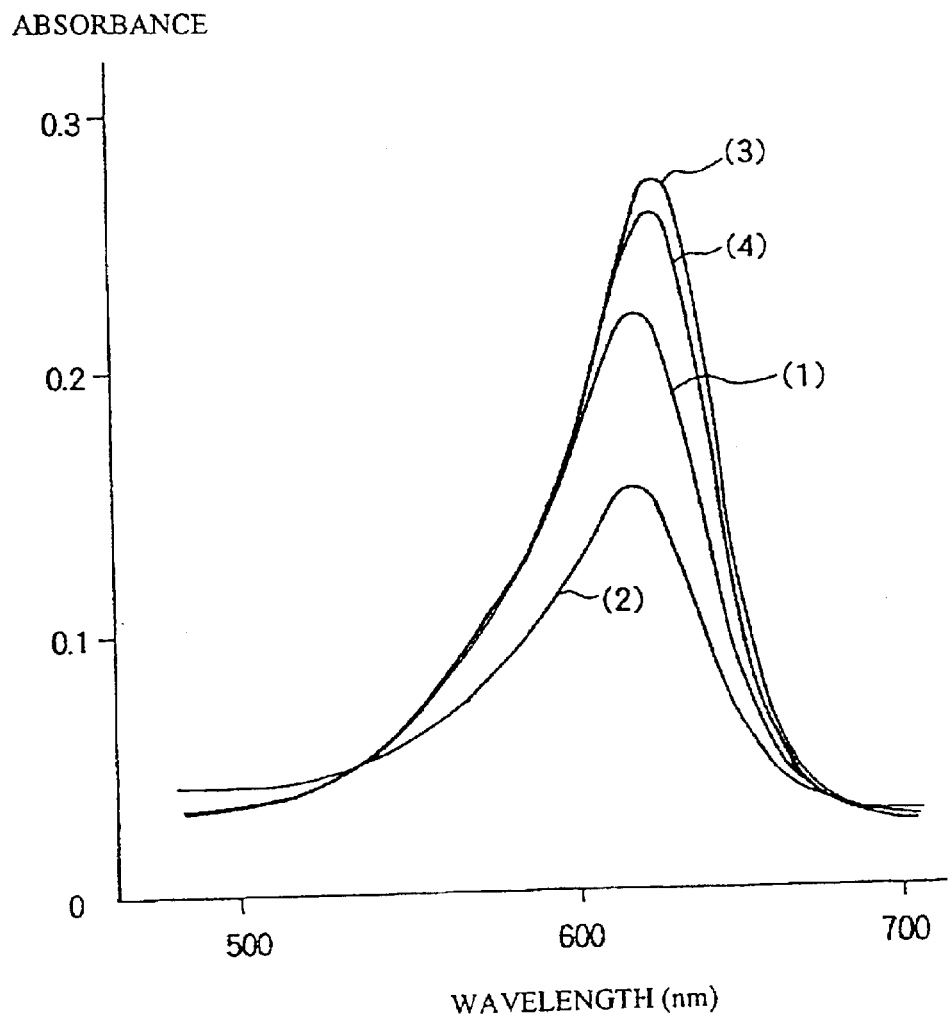
FIG. 3 represents absorption spectra of a mixture of an IgG fraction derived from the antiserum against hemocyanin labeled with Malachite Green according to this invention, and Malachite Green.

As is shown in FIG. 3, it is found that while the absorption spectrum of a mixed solution of MG and blank IgG displays no change from the spectrum of MG alone in the wavelength of its absorption maximum, a mixed solution of MG and the IgG fraction having the anti-MG-KLH activity displays the wavelength of its absorption maximum which has been shifted to a longer wavelength by 6–7 nm relative to the counterpart wavelength of MG alone.

This suggests that the IgG fraction having the anti-MG-KLH activity specifically binds to MG to form a complex which causes the electronic state of the dye to change and thereby shifts the wavelength of the absorption maximum.

(7) Fluorescence Spectra

The fluorescence spectrum of the aforementioned mixture was measured with a Hitachi Model 850 fluorescence spectrophotometer under the following conditions: an excitation wavelength of 617 nm; fluorescence wavelengths of 630–800 nm; a band-pass width of 5 nm at both excitation and emission sides; a scan speed of 60 nm/min; a time constant of 0.5 sec; and Low gain of a photomultiplier. See FIG. 4.

Figure 4:
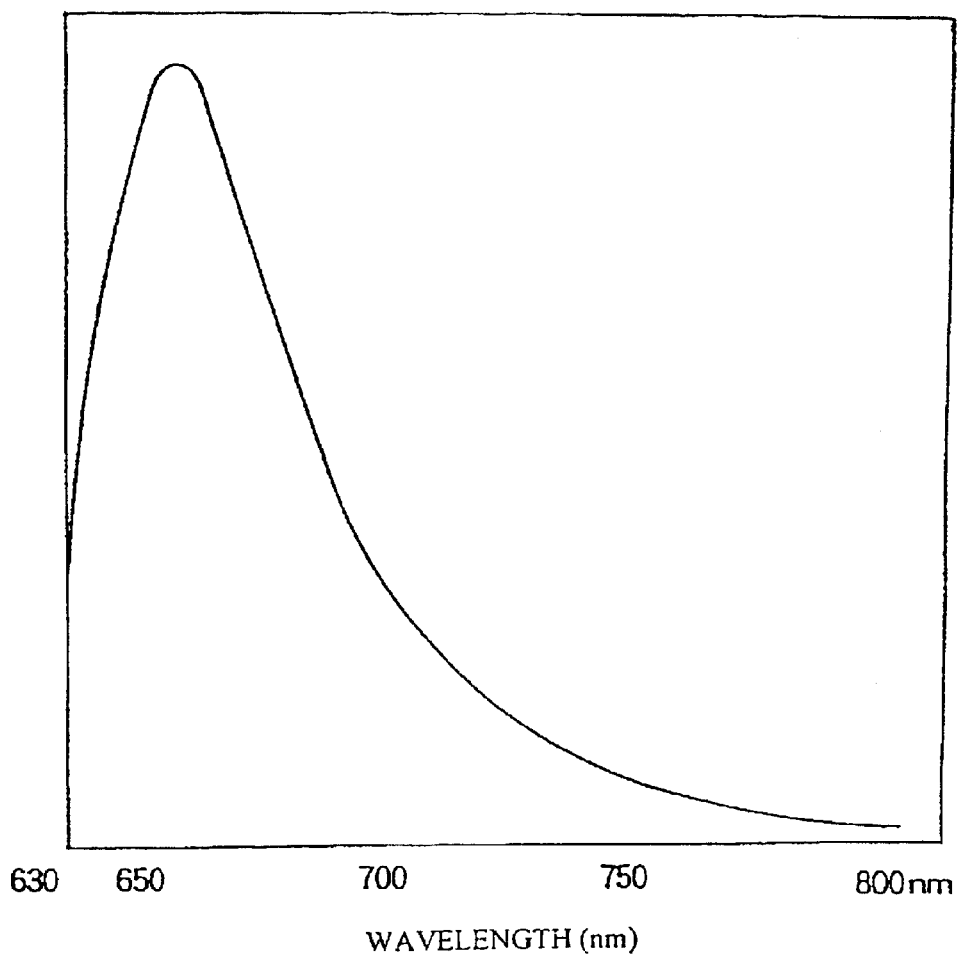
FIG. 4 represents differential fluorescence spectra of a mixture of the IgG fraction derived from the antiserum against hemocyanin labeled with Malachite Green according to this invention, and Malachite Green.

FIG. 4 illustrates a differential spectrum which has been obtained by subtracting the fluorescence spectrum of a mixed solution of blank IgG and MG from the fluorescence spectrum (excitation light of 617 nm, emission of 630–800 nm) of a mixed solution of MG and the IgG fraction having the anti-MG-KLH activity. Since the differential spectra can remove problematic noises in the fluorescence analysis such as the fluorescence of a cell itself and Raman scattering of a solvent, it becomes possible to obtain the fluorescence spectrum purely pertaining to a sample.

The differential spectrum clearly indicates that MG of the anti-MG-KLH IgG complex is fluorescent. Namely, it has been shown that MG, which is normally nonfluorescent, turns fluorescent owing to the specific formation of a complex with the antibody.

Accordingly, the procedures as described above will allow MG which has turned fluorescent to be analyzed fluorometrically in a specific, quantitative manner.

(8) Decreases in Background Fluorescence by Use of MG

As described below, an antibody directed against the subject substance to be detected was covalently labeled with MG, an anti-MG antibody was allowed to react with the aforementioned antibody, and then the fluorescence spectrum emitted was observed. Since this use of the anti-MG antibody decreased the background fluorescence, it was appreciated that MG which had labeled to the antibody was highly useful as a fluorescence label.

A sample where murine serum components had been bound to titer plates was prepared and the quantities of its background fluorescence, as well as its fluorescence spectra were measured to compare the case where the sample was excited by the excitation wavelength of MG with the case where the sample was excited by a shorter wavelength.

The procedures and results will be described in detail hereinafter.

(A) Use of MG as a Fluorescence Label in Fluoroimmuno Assays (i) Labeling Rabbit Anti-Mouse IgG Antibody with MG Rabbit anti-mouse IgG antibody (Wako Chemicals) 1.05 mg was dissolved in 0.5 ml of PBS (20 mM, pH 7.3), 9.5 ml of a 0.5 M carbonate buffer solution (pH 9.0) was added, and stirred. To this solution was added 0.3 mg of MGITC (Mp Inc.) dissolved in 40 $\mu$l of dimethyl sulfoxide (DMSO) to prepare a reaction mixture. This reaction mixture was stirred overnight at 4° C. under shielded light to allow MGITC to covalently react with IgG, completing the labeling.

The reaction mixture was subjected to gel filtration chromatography on a desalting column equilibrated with PBS (10 DG, Bio-Rad) by elution with PBS to remove unreacted MGITC. Thus, fraction of rabbit anti-mouse IgG antibody labeled with MG (hereinafter referred to as "MG-labeled antibody") was obtained.

Figure 9:
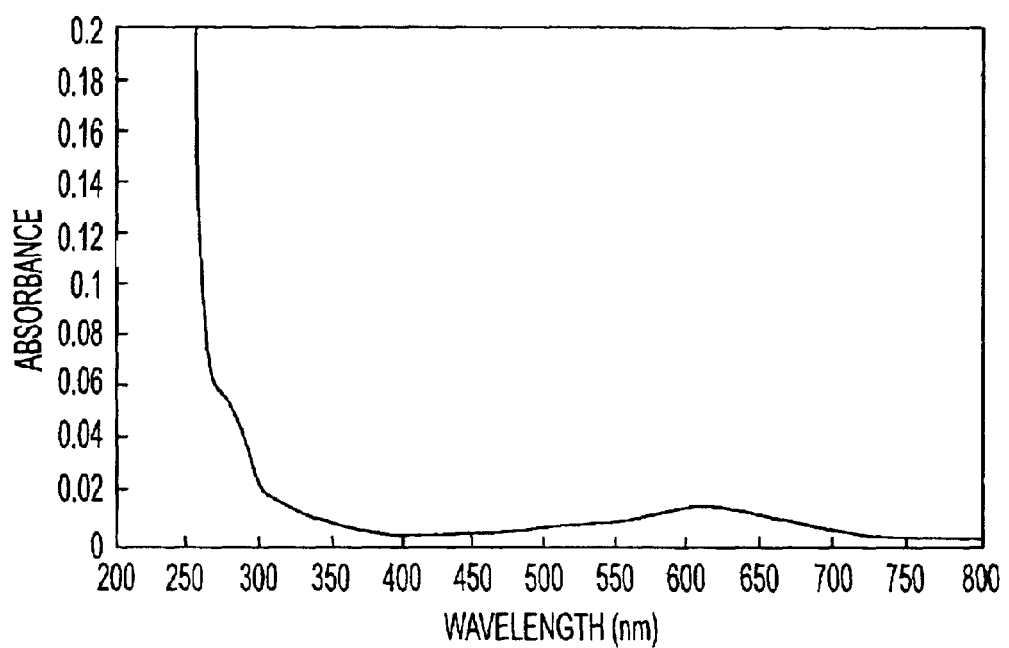
FIG. 9 represents an absorption spectrum of a rabbit anti-mouse IgG antibody labeled with Malachite Green according to this invention.

To 100 µl of this fraction was added 900 µl of PBS to give a 10-fold dilution of the fraction. The absorption spectrum of the dilution was measured with PBS as a control, and results are shown in FIG. 9. Since an absorption maximum was observed in the vicinity of 620 nm, it was ascertained that the antibody had been labeled with MG.

(ii) Reaction of MG-Labeled Antibody with Anti-MG Antibody and Fluorescence Spectra.

To a 100 µl fraction of the MG-labeled antibody as described above was added 5 µl of an anti-MG antibody fraction and 895 µl of PBS, and it was stirred for one hour at room temperature to sufficiently equilibrate the antigen-antibody reaction between MG and the anti-MG antibody.

Subsequently, the fluorescence spectrum of the above solution was measured with a Hitachi Model 850 fluorescence spectrophotometer under the following conditions: an excitation wavelength of 620 nm; emission wavelengths of between 630–750 nm; a band-pass width of 5.0 nm at both excitation and emission sides; a scan speed of 60 nm/min; and High gain of a photomultiplier.

Figure 10A:
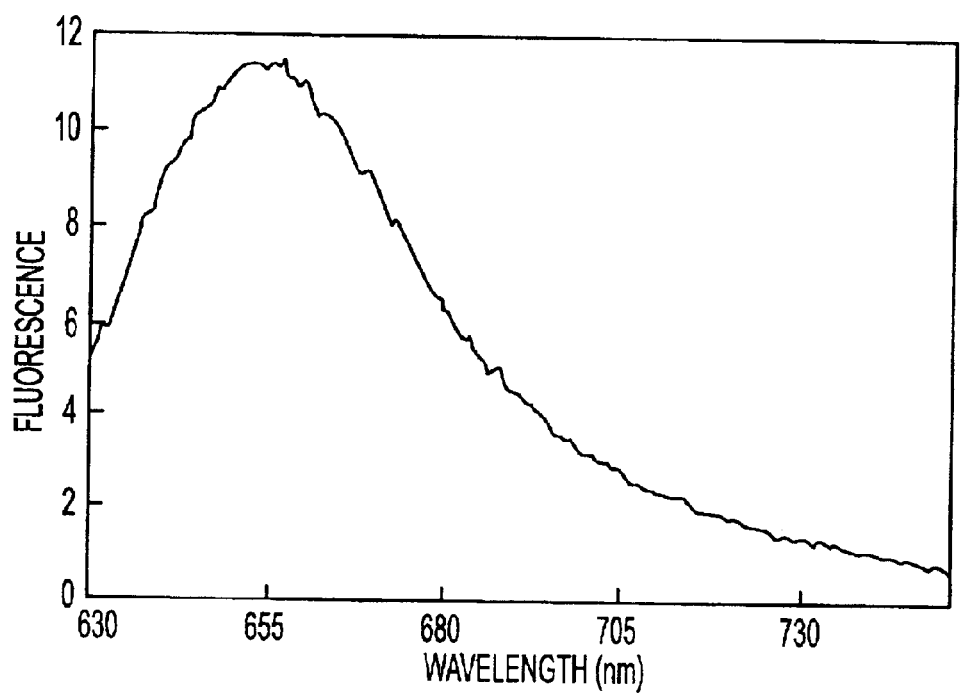
FIG. 10A represents a fluorescence spectrum of a rabbit anti-mouse IgG antibody labeled with Malachite Green when it has been reacted with an anti-MG antibody according to this invention.
Figure 10B:
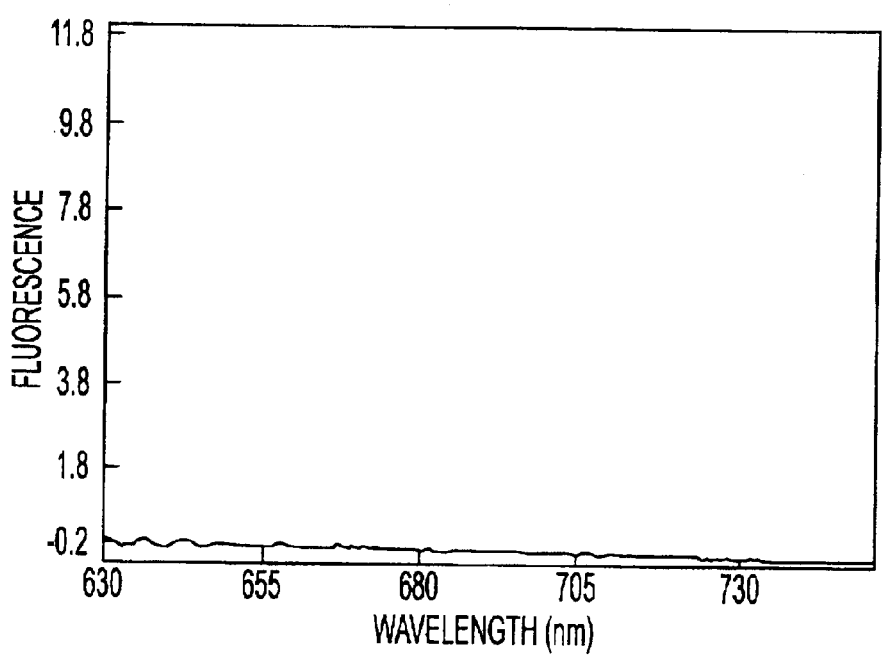
FIG. 10B represents a fluorescence spectrum of the rabbit anti-mouse IgG antibody labeled with Malachite Green when it has been reacted with a blank IgG.

The results are shown in FIG. 10A. Fluorescence having a maximal emission at between 650 nm and 660 nm was observed. This confirms that MG labeled on the antibody turned fluorescent. FIG. 10B illustrates that a fluorescence spectrum obtained by reaction of the MG-labeled antibody with a blank antibody (one that does not bind to MG) has little fluorescence intensity. This indicates that the reaction between the MG-labeled antibody and the anti-MG antibody is specific.

(B) Comparison of the Background Fluorescence Quantities of Sera (i) Preparation of Sera Blood was collected from a mouse (BALB/C, male adults) and was allowed to stand for 30 min at room temperature to coagulate. This was left overnight at 4° C., blood clots resulting from the coagulation of blood separated and an antiserum was collected therefrom.

(ii) Binding of Serum Components to Titer Plates

The mouse serum (50 µl) was added to each of 96 wells in a titer plate made of plastic (ELISA-PLATE Model F-form, available from Greiner) and the titer plate was allowed to stand for 6 hr at room temperature to let the serum components bind to the titer plate. Subsequently, each well of the titer plate was washed with a washing buffer containing PBS and 0.05% TWEEN 20 to remove the serum components that were not bound to the wells.

(iii) Measurement of Quantities of Background Fluorescence

Figure 11:
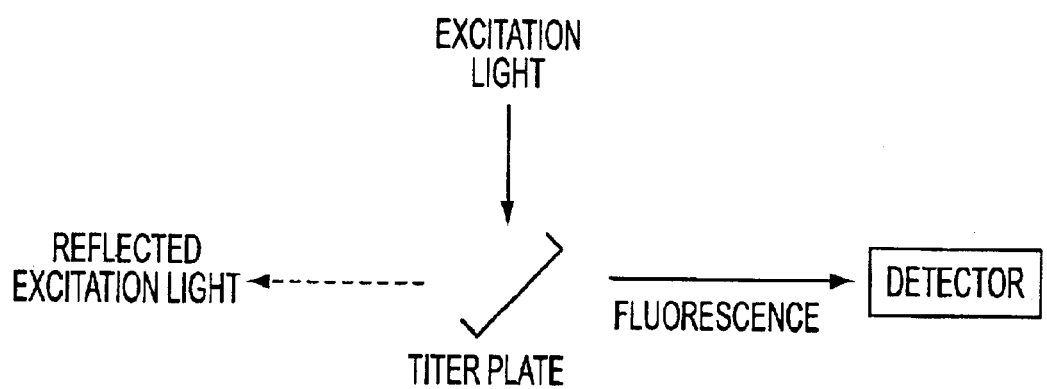
FIG. 11 schematically represents a configuration of the titer plate in a fluorescence spectrophotometer used for this invention.

The titer plate prepared according to the procedures as described in (B) was set in a cell holder of a Hitachi Model 850 fluorescence spectrophotometer. In so doing, the bottom of the titer plate was tilted 45 degrees with respect to both excitation light and a detector. See FIG. 11. With this configuration, the excitation light reflected by the bottom face of the titer plate is not allowed to directly enter the detector. Also, superfluous portions of the titer plate which would impair irradiation of the excitation light or fluorescence measurements were cut away in advance. The background fluorescence observed was a superimposition of fluorescence arising from serum components and that arising from the titer plate materials.

Figure 12A:
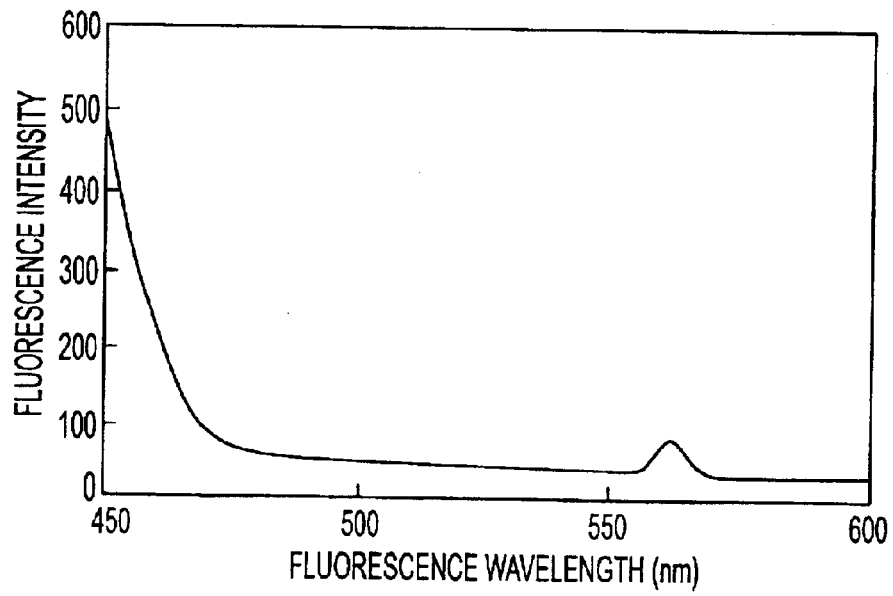
FIG. 12A represents a background fluorescence spectrum of the titer plate to which murine serum components are bound as measured with an excitation wavelength of 440 nm and fluorescence wavelengths of between 450 nm and 600 nm.
Figure 12B:
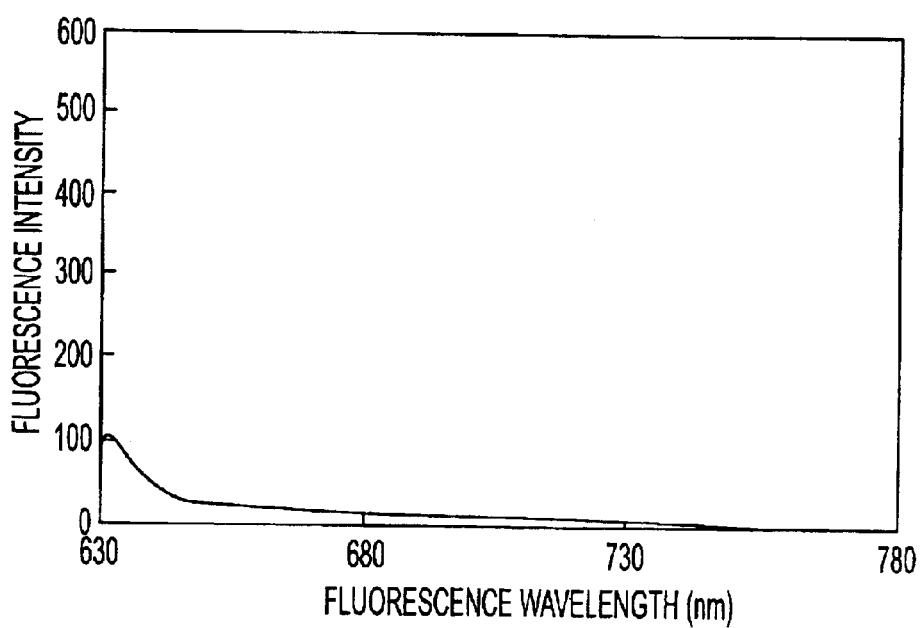
FIG. 12B represents a background fluorescence spectrum of the titer plate to which murine serum components are bound as measured with an excitation wavelength of 620 nm and fluorescence wavelengths of between 630 nm and 780 nm.

Measurement conditions are two types as follows:

a) an excitation wavelength of 440 nm, and fluorescence wavelength of between 450 nm and 600 nm (See FIG. 12A); and b) an excitation wavelength of 620 nm, and emission wavelengths of between 630 nm and 780 nm (See FIG. 12B). The conditions in a) are those used for the fluorescence measurement of CCJV (9-(2-carboxy-2-cyanovinyl) julolidine) and are also close to those used for the fluorescence measurement of fluorescein, a fluorescent dye which is commonly employed in fluoroimmuno assays; in the latter case, a maximal excitation wavelength of 483.5 nm and a maximal emission wavelength of 525 nm are used. See the Dictionary of Biochemistry cited supra; p. 1091. The results of measurements clearly indicates that in the case of b) the quantity of the background fluorescence is markedly reduced as compared with case a) where excitation at 440 nm is employed.

As results described above manifest, it is concluded that use of MG in the fluorescence measurement can reduce the background level to a great extent as compared with the use of CCJV or fluorescein with the advantage of enabling higher sensitivity in measurement.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application No. 72426/1996 filed on Mar. 27, 1996 is hereby incorporated by reference.

What is claimed is:

1. An antiserum comprising an antibody directed against an antigen formed by conjugation of an immunogenic substance with a dye selected from the group consisting of dyes each having a triphenylmethane moiety and dyes each having a diphenylmethane moiety;

wherein the dye is nonfluorescent when said antibody and said dye are in non-complexed form, and is fluorescent upon complexation of said antibody with said dye.

2. The antiserum according to claim 1, wherein the immunogenic substance is at least one member selected from the group consisting of bovine serum albumin, human serum albumin, egg albumin, bovine γ globulin, equine serum globulin, human γ globulin, ovine γ globulin, bovine thyroglobulin, porcine thyroglobulin and hemocyanin.

3. The antiserum according to claim 1, wherein a fluorescence quantum yield of the dye when said dye is fluorescent is more than 100 times as large as that of the dye when said dye is nonfluorescent.

4. The antiserum according to claim 1, wherein the dye is Auramine O.

5. An IgG fraction of an antiserum comprising an antibody directed against an antigen formed by conjugation of an immunogenic substance with a dye selected from the group consisting of dyes each having a triphenylmethane moiety and dyes each having a diphenylmethane moiety;

wherein the dye is nonfluorescent when said antibody and said dye are in non-complexed form, and is fluorescent upon complexation of said antibody with said dye.

6. The IgG fraction according to claim 5, wherein the immunogenic substance is at least one member selected from the group consisting of bovine serum albumin, human serum albumin, egg albumin, bovine γ globulin, equine serum globulin, human γ globulin, ovine γ globulin, bovine thyroglobulin, porcine thyroglobuline and hemocyanin.

7. The IgG fraction according to claim 5, wherein a fluorescence quantum yield of the dye when said dye is fluorescent is more than 100 times as large as that of the dye when said dye is nonfluorescent.

8. The IgG fraction according to claim 5, wherein the dye is Auramine O.

9. A composition comprising an antibody directed against an antigen formed by conjugation of an immunogenic substance with a dye selected from the group consisting of dyes each having a triphenylmethane moiety and dyes each having a diphenylmethane moiety;

wherein the dye is nonfluorescent when said antibody and said dye are in non-complexed form, and is fluorescent upon complexation of said antibody with said dye.

10. The composition according to claim 7, wherein the immunogenic substance is at least one member selected from the group consisting of bovine serum albumin, human serum albumin, egg albumin, bovine γ globulin, equine serum globulin, human γ globulin, ovine γ globulin, bovine thyroglobulin, porcine thyroglobulin and hemocyanin.

11. The composition according to claim 7, wherein a fluorescence quantum yield of the dye when said dye is fluorescent is more than 100 times as large as that of the dye when said dye is nonfluorescent.

12. The composition according to claim 7, wherein the dye is Auramine O.

* * * * *